United States Patent [19]
VanBeek et al.

[11] Patent Number: 5,882,353
[45] Date of Patent: *Mar. 16, 1999

[54] MECHANICAL TISSUE EXPANDER

[75] Inventors: Allen L. VanBeek, Edina; Alfred Abner Iversen, Wayzata, both of Minn.

[73] Assignee: PMT Corporation, Chanhassen, Minn.

[ * ] Notice: The terminal 81 months of this patent has been disclaimed.

[21] Appl. No.: 225,884

[22] Filed: Apr. 11, 1994

[51] Int. Cl.$^6$ .................................................... A61F 2/12
[52] U.S. Cl. .................................................................. 623/8
[58] Field of Search ............................. 623/7, 8, 11, 26; 606/191; 128/899

[56] References Cited

U.S. PATENT DOCUMENTS

| | | | |
|---|---|---|---|
| 4,243,037 | 1/1981 | Smith | 606/191 X |
| 4,449,532 | 5/1984 | Storz | 606/191 X |
| 4,662,357 | 5/1987 | Pierce et al. | 128/899 X |
| 4,666,447 | 5/1987 | Smith et al. | 623/8 |
| 4,862,891 | 9/1989 | Smith | 606/191 X |
| 5,021,064 | 6/1991 | Caines | 623/26 |
| 5,074,878 | 12/1991 | Bark et al. | 623/8 |
| 5,092,348 | 3/1992 | Dubrul et al. | 128/899 |
| 5,236,460 | 8/1993 | Barber | 623/17 |

OTHER PUBLICATIONS

Rees, Thomas D. et al. "The Use of Inflatable Breast Implants" *Plastic and Reconstructive Surgery,* Dec. 1973.

Becker, Hilton. Breast Reconstruction Using an Inflatable Breast Implant with Detachable Reservoir. *Plastic and Reconstructive Surgery,* Apr. 1984.

Herman, Steven. "The Meme Implant" *Plastic and Reconstructive Surgery, Mar. 1984.* Mentor brochure for The Becker Expander/Mammary Prosthesis, Nov. 1987.

*Primary Examiner*—Michael J. Milano

[57] ABSTRACT

The invention relates to a mechanical tissue expansion device for use in the reconstruction or augmentation of a portion of an individual's body. The invention includes a pair of tissue expansion plates which may be substantially flat or which may include an arcuate curved shape. Each of the tissue expansion plates has a plurality of apertures therethrough in order to facilitate the ingrowth of natural tissue within an enlarged cavity. The tissue expansion plates are mechanically separated by a means for expansion which preferably includes a cylinder having three telescopically expanding rods engaged thereto. The means for expansion is incrementally regulated by an operating means. The operating means preferably includes tubing engaged to the cylinder and to a port having a silicone membrane, for receipt of incremental portions of saline solution or water for telescopic expansion of the rods from the cylinder. In alternative embodiments, the means for expansion may include a rotatable flexible threaded arm for expansion of the rods from the cylinder, a worm gear engaged to a keyed-threaded surface for expansion of the rods from the cylinder, or a hydraulic cylinder engaged to expansible linkages for separation of the tissue expansion plates from each other. In the alternative embodiments, the operating means may include motors, batteries, drive shafts, and various gears for incremental enlargement of the means for expansion.

13 Claims, 5 Drawing Sheets

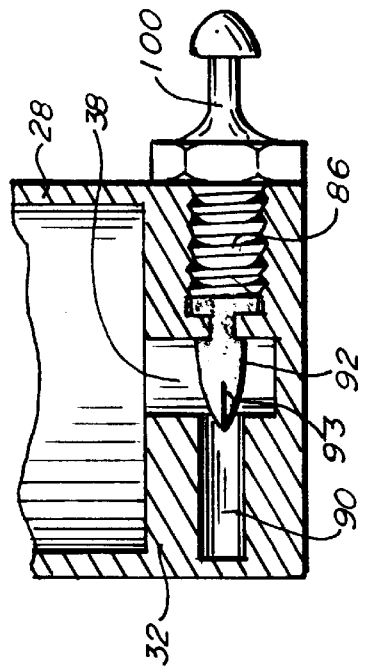
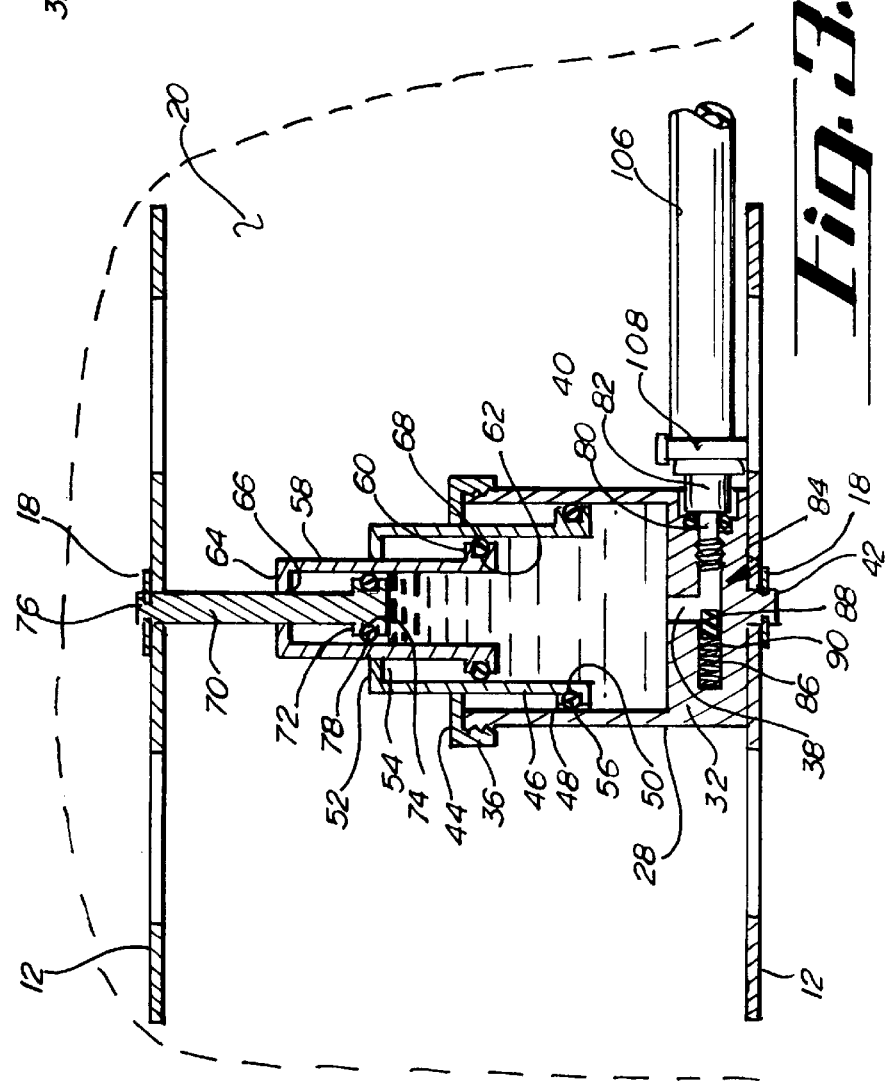

MECHANICAL TISSUE EXPANDER

BACKGROUND OF THE INVENTION

In the past, numerous medical procedures and devices have been utilized for breast reconstruction and/or cosmetic augmentation. The prior art as known has primarily involved the surgical application/introduction of tissue expansion devices for use with silicone breast implants within an individual. In the past, a tissue expander was used to create a pocket or cavity within the breast area of an individual which created a void upon removal of the expander. A prosthetic implant was then used to fill this void. The implanted materials utilized were generally retained inside an individual's body for an extended or indefinite period of time.

An implanted shell of silicone material and/or a bladder containing silicone gel may adversely affect the health or appearance of a person due to tissue rejection, contracture, or infection. A problem of breast reconstruction and/or augmentation involves the encapsulation of an implant within a sheet of fibrous tissue, and the subsequent capsular contraction of the "fibrous capsule". The encapsulation of an implant occurs as a natural defensive mechanism of an individual for protection against a foreign material within the body. The encapsulation of an implant prosthesis, in and of itself, is nonproblematic. The capsular contraction of a "fibrous capsule" surrounding an implant prosthesis causes firmness around, and compression of, the implant which in turn may cause discomfort. In addition, the capsular contraction of a "fibrous capsule" may cause an implant to compress to a nearly spherical or unnatural shape causing an undesirable and embarrassing appearance for an individual. Another problem of reconstruction or augmentation devices involved leaks, breaks, and/or biological infection associated with implanted materials.

The present invention eliminates these problems by the mechanical and incremental expansion of the existing mammary tissue of an individual for a relatively short duration of time, and either allowing a person's natural tissue to expand into the enlarged cavity, or transferring tissue from another area of the body into the cavity for augmentation or reconstruction of a breast. The elimination of permanent prosthetic devices reduces the risk of health related problems for an individual. The problems of leakage, breakage, rejection, and/or capsular contracture around artificial or foreign substances is thereby eradicated.

This invention relates to a mechanical tissue expansion device suitably for use in breast reconstruction, breast augmentation, or wherever tissue needs to be expanded. The present invention incrementally expands existing tissue, establishing a cavity or void which is adapted for ingrowth or receipt of a person's natural fatty, glandular, or mammary tissue. Following the ingrowth of the cavity or void with an individual's natural tissue, the invention may be disassembled and removed. No artificial implants or foreign objects are retained within an individual's body which may later cause rejection or problems. The health and safety of an individual is thereby significantly improved as compared to tissue expansion and implant devices as known.

SUMMARY OF THE INVENTION

The invention relates to a mechanical tissue expansion device for use in the reconstruction or augmentation of a portion of an individual's body. The invention includes a pair of tissue expansion plates which may be substantially flat or which may include an arcuate curved shape. Each of the tissue expansion plates has a plurality of apertures therethrough in order to facilitate the ingrowth of natural tissue within an enlarged cavity. The tissue expansion plates are mechanically separated by a means for expansion which preferably includes a cylinder having three telescopically expanding rods engaged thereto. The means for expansion is incrementally regulated by an operating means. The operating means preferably includes tubing engaged to the cylinder and to a port having a silicone membrane, for receipt of incremental portions of saline solution or water for telescopic expansion of the rods from the cylinder. In alternative embodiments, the means for expansion may include a rotatable flexible threaded arm for expansion of the rods from the cylinder, a worm gear engaged to a keyed-threaded surface for expansion of the rods from the cylinder, or a hydraulic cylinder engaged to expansible linkages for separation of the tissue expansion plates from each other. In the alternative embodiments, the operating means may include motors, batteries, drive shafts, and various gears for incremental enlargement of the means for expansion.

It is a primary object of the present invention to provide a removable mechanical tissue augmentation or reconstruction appliance of relatively simple and inexpensive design, construction, and operation which is durable and safe, and which fulfills its intended purpose without fear of short or long term injuries to persons.

It is another object of the present invention to expand existing mammary tissue for establishment of a cavity or void which may be naturally filled by ingrowth of an individual's own fatty, granular, fibrous, muscle or mammary tissue without the necessity of using artificial silicone membranes or permanent prosthetic devices.

It is still another object of the present invention to provide a removable mechanical tissue expansion appliance which may be quickly, efficiently and easily assembled or disassembled within the existing tissue of an individual.

It is still another object of the present invention to provide flexibility to an individual by the provision of a mechanism for incrementally expanding the existing mammary tissue for personal selection of a desired level of augmentation or reconstruction.

A feature of the present invention includes a pair of tissue expansion plates having a plurality of apertures for facilitating the ingrowth of existing mammary, glandular, or fatty tissue through the expansion plates, and around the expanding appliance, within a breast being reconstructed or augmented.

Another feature of the present invention includes a means for expansion including a cylinder having at least one telescopically mounted rod for separating the pair of tissue expansion plates and expanding the existing mammary tissue of a breast being reconstructed and/or augmented.

Still another feature of the present invention includes an operating means having tubing and a silicone membrane for incremental receipt of saline solution or water for telescopic expansion of the rods from the cylinder.

Still another feature of the present invention includes a cylinder having a channel, a one-way valve, and a spring for communication with the operating means.

Still another feature of the present invention includes a cylinder having a channel and either a duck-bill-type or an umbrella-type of one-way valve for communication with the operating means.

Still another feature of the present invention includes a means for expansion having a rotatably flexible threaded arm engaged to a rod, a motor, a drive shaft, and a gear for incrementally separating the tissue expansion plates and enlarging an individual's existing mammary tissue.

Still another feature of the present invention includes a means for expansion having a keyed-threaded surface, a worm gear engaged to the keyed-threaded surface, a spur gear engaged to the worm gear, a shaft, and a motor for incrementally separating the tissue expansion plates and enlarging an individual's existing mammary tissue.

Still another feature of the present invention includes a means for expansion having an expandable hydraulic cylinder telescopically engaged to a pair of expansible linkages for incremental enlargement of an individual's existing mammary tissue.

BRIEF DESCRIPTION OF THE DRAWINGS

FIG. 3 is a cross sectional side view of the invention as expanded taken along the line 2—2 of FIG. 1 showing a one-way check valve and tissue expansion.

FIG. 4 is a detail view of a duckbill valve.

DETAILED SPECIFICATION OF THE PREFERRED EMBODIMENT

Figure 1:
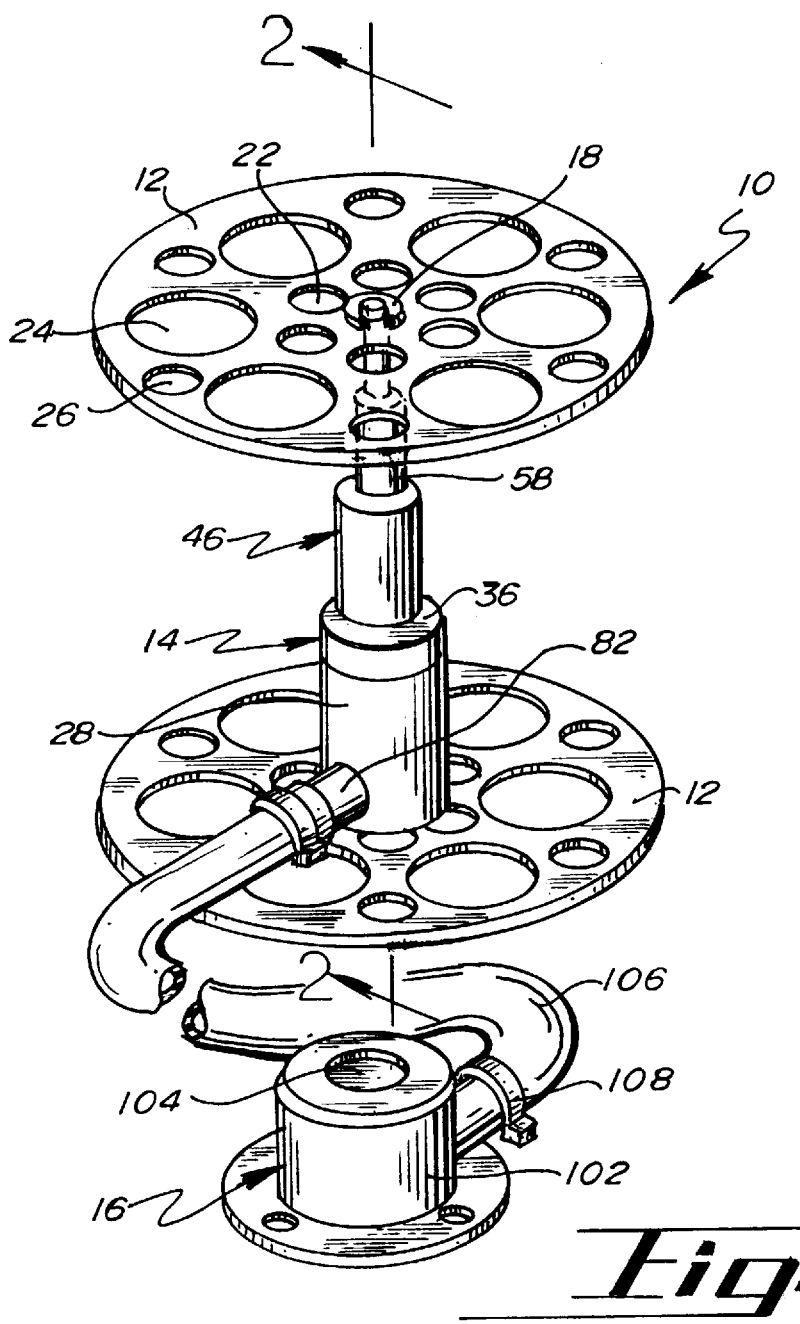
FIG. 1 is an isometric view of the invention.

A number of embodiments of the invention are illustrated and described herein. In general, the removable mechanical tissue expansion appliance is indicated by the numeral 10. The removable mechanical tissue expansion appliance 10 in general includes a pair of tissue expansion plates 12, a means for expansion 14, and an operating means 16. The operation of the removable mechanical tissue expansion appliance 10 is described herein for use in the reconstruction and/or augmentation of a breast of an individual. The invention may be suitably used for expansion and reconstruction or repair of other damaged tissue areas of an individual and is not limited to exclusive use in the reconstruction or augmentation of an individual's breast.

The pair of tissue expansion plates 12 are preferably affixed to opposite portions of the means for expansion 14 by removable retaining rings 18. (FIG. 1) The pair of tissue expansion plates 12 are preferably positioned within a breast such that one tissue plate 12 is positioned proximal to a person's ribs and functions as a base during the incremental expansion of the removable mechanical tissue expansion appliance 10. The other tissue expansion plate 12 functions to incrementally separate mammary tissue from a body for incremental enlargement of the cavity 20.

The pair of tissue expansion plates 12 are preferably formed of a stainless steel metal material. The material selected for the pair of tissue expansion plates 12 may include, but is not limited to, metals and/or rigid plastics provided that the essential functions, features and attributes described herein are not sacrificed. The pair of tissue expansion plates 12 should be formed of a sufficiently rigid material to avoid bending, fracture, or failure during the incremental enlargement of the cavity 20.

The pair of tissue expansion plates 12 are preferably circular in shape. Alternatively, the pair of tissue expansion plates 12 may be oval-shaped at the preference of an individual. Each of the pair of tissue expansion plates 12 preferably has a diameter dimension approximating 2.75 inches and a thickness dimension approximating 0.023 inches. It should be noted that the dimensions provided herein may be significantly increased or decreased at the preference of an individual depending upon the material selected and the area of a body to be medically reconstructed or augmented. It should be apparent that either larger or smaller tissue expansion plates may be used dependent upon the size of the individual. In the preferred embodiment, the pair of tissue expansion plates 12 are flat. Alternatively, the tissue expansion plates 12 may include an arcuate shape for minimizing the risk of laceration of internal mammary tissue. The edges of the pair of tissue expansion plates 12 may also be rounded at the preference of an individual.

Each of the tissue expansion plates 12 includes a plurality of apertures therethrough. A plurality of first apertures 22 encircle the center point of a tissue expansion plate 12. The plurality of first apertures 22 are preferably located outwardly from the center of a tissue expansion plate 12, a radius dimension approximating 0.750 inches. Each of the first apertures 22 preferably has a diameter dimension approximating 0.25 inches and is preferably symmetrically positioned about the center of a tissue expansion plate 12 as seen in FIG. 1. In the preferred embodiment, the number of first apertures 22 approximates six in number. It should be noted that the number of first apertures 22 may be significantly increased or decreased at the preference of an individual provided the essential functions, features and attributes described herein are not sacrificed.

A plurality of second apertures 24 preferably encircle the center of a tissue expansion plate 12. The second apertures 24 are preferably located outwardly from the center of a tissue expansion plate 12, a radius distance approximating 1.75 inches. Each of the second apertures 24 preferably has a diameter dimension approximating 0.625 inches and are preferably symmetrically positioned about the center of a tissue expansion plate 12 as seen in FIG. 1. In the preferred embodiment, the number of second apertures 24 approximates six in number. It should be noted that the number of second apertures 24 may be significantly increased or decreased at the preference of an individual.

A plurality of third apertures 26 preferably encircle the center of a tissue expansion plate 12. The plurality of third apertures 26 are preferably located outwardly from the center of a tissue expansion plate 12, a radius distance approximating 2.25 inches. In the preferred embodiment, each of the plurality of third apertures 26 has a diameter dimension approximating 0.25 inches and is symmetrically positioned from the center of a tissue expansion plate 12, where each of the third apertures 26 is preferably positioned equal distances between two of the second apertures 24, and in substantial alignment to a first aperture 22. In the preferred embodiment, the number of third apertures 26 approximates six in number. It should be noted that the number of third apertures 26 may be significantly increased or decreased at the preference of an individual without adversely affecting the performance of a tissue expansion plate 12.

A purpose of the first, second and third apertures 22, 24, and 26, respectively, is to permit the ingrowth of natural tissue within the cavity 20. It should be noted that the natural tissue filling the cavity 20 may be mammary tissue, gland tissue, fatty tissue, muscle, or other natural tissue. For the purposes of the operation of the removable mechanical tissue expansion appliance 10, the type of tissue ingrowing within the cavity 20 is irrelevant for successful operation of the device. Upon the filling of the cavity 20 with natural ingrown tissue, the removable mechanical tissue expansion appliance 10 may be surgically removed from an individual. Another purpose of the first, second and third apertures 22, 24, 26, respectively, is to provide a surgeon with an area for application of sutures for affixation of a tissue expansion plate 12 in a desired location within an individual. Slippage of the removable mechanical tissue expansion appliance 10 is thereby avoided.

The pair of tissue expansion plates 12 preferably provide the means for the incremental enlargement of an individual's natural mammary tissue during the reconstruction or augmentation of an individual's breast.

It should be noted that the dimensions provided for the pair of tissue expansion plates 12 may be suitably increased or decreased at the preference of a physician. A tissue expansion plate 12 may be easily substituted for one of larger or smaller dimensions by removal of the retaining ring 18 and substitution of an alternate sized tissue expansion plate 12. It should be noted that any shape or type of tissue expansion plate 12 may be used as a portion of the removable mechanical tissue expansion appliance 10 at the preference of an individual.

The means for expansion 14 preferably functions to separate the pair of tissue expansion plates 12 for incremental expansion of mammary tissue. The means for expansion 14, in general, includes a cylinder 28 having a plurality of telescoping rods engaged thereto. In the preferred embodiment, the cylinder 28 and plurality of telescoping rods comprise the means for expansion 14.

The cylinder 28 is preferably of a hydraulic design. The cylinder 28 includes a base portion 32 and a threaded upper exterior surface which is suitably adapted for receiving engagement of a threaded cap 36.

The cylinder 28 is preferably formed of a sturdy stainless steel metal material. Alternatively, the cylinder 28 may be formed of any metal or plastic material as preferred by an individual provided that the essential functions, features, and attributes described herein are not sacrificed. It should be noted that the cylinder 28 should be formed of a sufficiently durable material to not fracture, break, or fail during the telescopic expansion of the rods upon exposure to hydraulic pressures approximating ten psi.

In the preferred embodiment, the vertical dimension of the cylinder 28 preferably approximates 0.775 inches and the vertical dimension of the base portion 32 preferably approximates 0.35 inches. The internal diameter dimension of the cylinder 28 preferably approximates 0.612 inches, and the outer diameter dimension preferably approximates 0.6875 inches. The base portion 32 preferably includes a channel 38 having a diameter dimension approximating 0.125 inches. The base portion 32 includes a lip 40 which is located proximal to the cylinder 28. The lip 40 has a width dimension approximating 0.040 inches. The lip 40 provides a surface for receiving engagement of the operating means 16 for engagement to the channel 38. It should be noted that the channel 38 may have any dimension as preferred by an individual, and preferably is equal to or exceeds 0.125 inches in diameter.

The cylinder 28 preferably functions to enclose a plurality of rods for telescopic expansion therefrom during the incremental expansion of mammary tissue for enlargement of the cavity 20. It should be noted that the base portion 32 of the cylinder 28 preferably includes a downwardly extending tab 42. (FIGS. 2 and 3) The tab 42 preferably extends from the base portion 32 an approximate distance of 0.20 inches. The tab 42 is preferably adapted for receiving engagement of one of the tissue expansion plates 12, which is attached thereto by a retaining ring 18. The cylinder 28 is preferably of sufficient strength and durability to withstand internal hydraulic pressure for expansion of the rods during the enlargement of the cavity 20. In addition, the cylinder 28 is preferably formed of one-piece construction and is preferably sealed, confining the saline solution or water which is used for expansion of the rods from the cylinder 28.

The threaded cap 36 is preferably engaged to the threaded upper exterior surface of the cylinder 28. The threaded cap 36 is preferably cylindrical in shape having a vertical width dimension approximating 0.25 inches. The threaded cap 36 preferably has an exterior diameter dimension approximating 0.750 inches and centrally positioned aperture therethrough. The threaded cap 36 preferably has a first circular ledge 44. The width of the first circular ledge 44 is preferably the difference between the inner diameter dimension of the cylinder 28 which approximates 0.612 inches, and the diameter dimension of the aperture which approximates 0.501 inches, for a difference approximating 0.111 inches. The threaded cap 36 is preferably engaged over the top of the cylinder 28. The threaded cap 36 is adapted for sealing of the cylinder 28 with respect to the rods. The first circular ledge 44 functions as a stop limiting the vertical expansion of one of the telescoping rods from the cylinder 28.

A first rod 46 is preferably centrally positioned within the cylinder 28, passing through the threaded cap 36. The first rod 46 preferably has an overall vertical dimension approximating 0.80 inches. The first rod 46 is preferably cylindrical in shape having a first platform 48 having a first channel 50, and a first top portion 52 having a centrally positioned aperture therethrough, which in turn defines a second circular ledge 54. The exterior diameter dimension of the first platform 48 preferably approximates 0.611 inches. The interior diameter dimension of the first platform preferably approximates 0.4245 inches. The width of the first channel 50 preferably approximates 0.081 inches. An approximate width dimension of 0.030 inches is provided for the first platform 48 above and below the first channel 50. Preferably the outer diameter dimension for the first rod 46 approximates 0.500 inches, and the inner diameter dimension approximates 0.4245 inches. The centrally positioned aperture through the first top portion 52 preferably has an approximate diameter dimension of 0.313 inches. The approximate thickness of the first top portion 52 is 0.025 inches. The width of the second circular ledge 54 preferably approximates 0.1115 inches.

A first O-ring 56 is preferably positioned within the first channel 50. The first O-ring 56 preferably has an inner diameter dimension approximating one-half inch and an outer diameter dimension approximating five-eighths inches. It should be noted that the first O-ring 56 encircles the first platform 48 and is preferably securely engaged within the first channel 50.

The first platform 48 and the first O-ring 56 are preferably adapted for flush and sealing engagement to the interior wall of the cylinder 28. The first rod 46 is preferably adapted for vertical movement within the cylinder 28, and is limited in vertical expansion by the engagement between the first platform 48 and the first circular ledge 44 of the threaded cap 36. During the introduction of saline solution or water into the cylinder 28, the first rod 46 expands vertically upward due to the internal pressure of the fluid. It should be noted that the first platform 48 and the first O-ring 56 provide a seal against the interior of the cylinder 28 preventing saline solution or water from leaking from the means for expansion 14.

Figure 2:
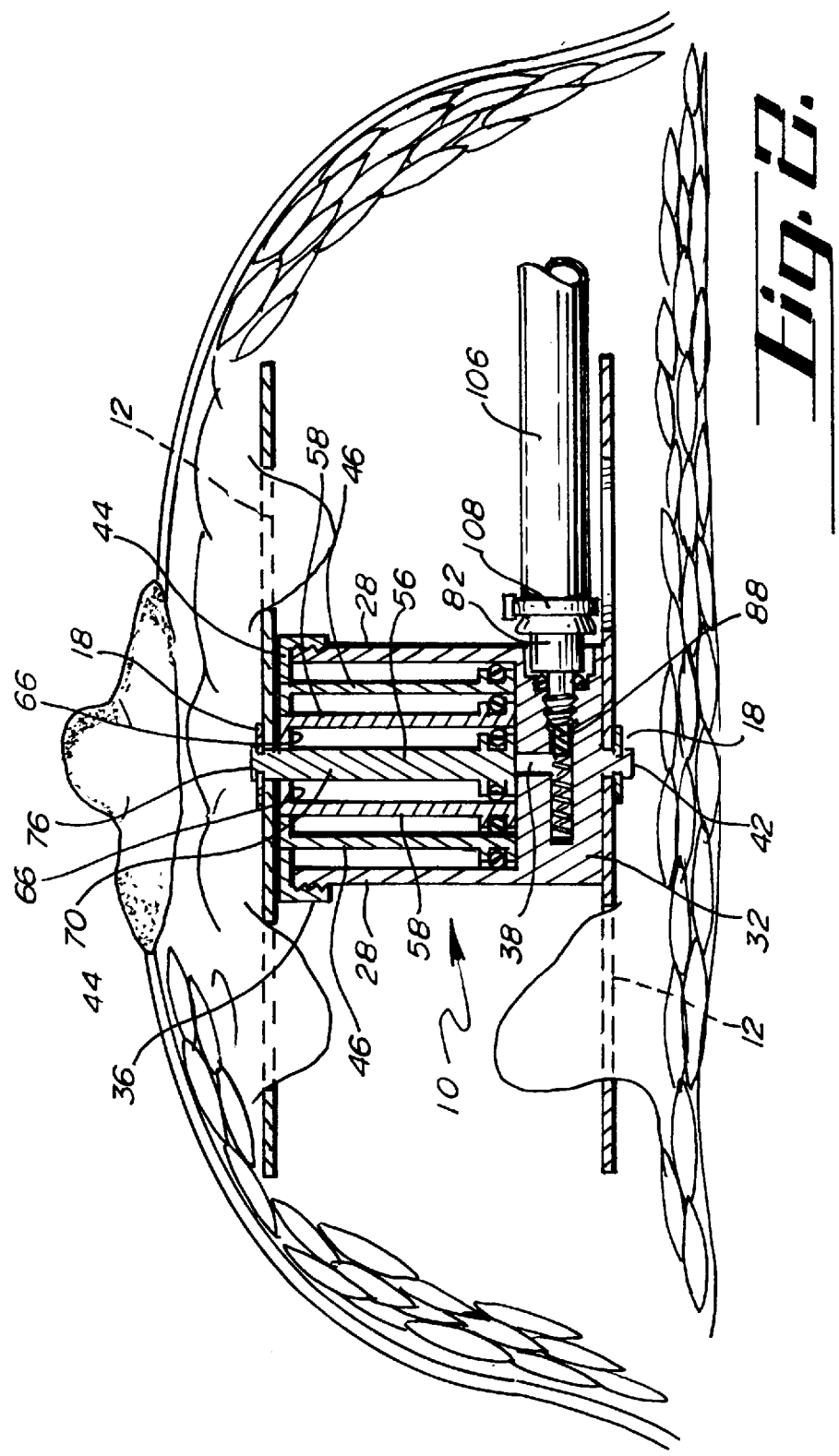
FIG. 2 is an environmental cross sectional side view of the invention taken along line 2—2 of FIG. 1 showing the invention in a retracted position prior to expansion for reconstruction and/or augmentation suitably within a breast.

As seen in FIG. 2, the first platform 48 and first O-ring 56 are adapted for engagement to the interior wall of the cylinder 28, and the base portion 32, when the mechanical tissue expansion appliance 10 is fully retracted for insertion into, or removal from, an individual during reconstruction or augmentation of an individual's tissue.

A second rod 58 is preferably centrally positioned within the cylinder 28 and the first rod 46, passing through the first top portion 52. The second rod 58 preferably has an overall vertical dimension approximating 0.80 inches. The second rod 58 is preferably cylindrical in shape having a second platform 60 having a second channel 62, and a second top portion 64 having a centrally positioned aperture therethrough, which in turn defines a third circular ledge 66. The exterior diameter dimension of the second platform 60 preferably approximates 0.4235 inches. The interior diameter dimension of the second platform 60 preferably approximates 0.237 inches. The width of the second channel 62 preferably approximates 0.081 inches. An approximate width dimension of 0.030 inches is provided for the second platform 60 above and below the second channel 62. Preferably the outer diameter dimension for the second rod 58 approximates five-sixteenths inches, and the inner diameter dimension approximates 0.237 inches. The centrally positioned aperture through the second top portion 64 preferably has an approximate diameter dimension of 0.126 inches. The approximate thickness of the second top portion 64 is 0.25 inches. The width of the third circular ledge 66 preferably approximates 0.111 inches.

A second O-ring 68 is preferably positioned within the second channel 62. The second O-ring 68 preferably has an inner diameter dimension approximating five-sixteenths of an inch and an outer diameter dimension approximating seven-sixteenths of an inch. It should be noted that the second O-ring 68 encircles the second platform 60 and is preferably securely engaged within the second channel 62.

The second platform 60 and the second O-ring 68 are preferably adapted for flush and sealing engagement to the interior wall of the first rod 46. The second rod 58 is preferably adapted for vertical movement within the cylinder 28 and the first rod 46, and is limited in vertical expansion by the engagement between the second platform 60 and the second circular ledge 54 of the first top portion 52. During the introduction of saline solution or water into the cylinder 28, the second rod 58 expands vertically upward due to the internal pressure of the fluid. The vertical expansion of the second rod 58 is terminated upon the engagement between the second platform 60 and the second circular ledge 54. It should be noted that the second platform 60 and the second O-ring 68 provide a seal against the interior of the first rod 46 preventing saline solution or water from leaking from the means for expansion 14. It should also be noted that the first rod 46 functions as a cylinder, confining the expansion of the second rod 58 during use of the mechanical tissue expansion appliance 10.

As seen in FIG. 2, the second platform 60 and second O-ring 68 are adapted for engagement to the interior wall of the first rod 46 and the base portion 32 when the mechanical tissue expansion appliance 10 is in its fully retracted or non-expanded position.

A third rod 70 is preferably centrally positioned within the cylinder 28 and the second rod 58, passing through the second top portion 64. The third rod 70 preferably has an overall vertical dimension approximating 0.80 inches. The third rod 70 is preferably cylindrical in shape, having a third platform 72 having a third channel 74, and a second tab portion 76. The exterior diameter dimension of the third platform 72 preferably approximates 0.236 inches, and the interior diameter dimension preferably approximates 0.125 inches. The width of the third channel 74 preferably approximates 0.081 inches. An approximate preferred width dimension of 0.030 inches is provided for the third platform 72 above and below the third channel 74. Preferably the outer diameter dimension for the third rod 70 approximates 0.125 inches, and the inner diameter dimension approximates 0.07 inches.

A third O-ring 78 is preferably positioned within the third channel 74. The third O-ring 78 preferably has an interior diameter dimension approximating one-eighth inch and an outer diameter dimension approximating one-quarter inch. It should be noted that the third O-ring 78 encircles the third platform 72 and is preferably securely engaged within the third channel 74.

The third platform 72 and the third O-ring 78 are preferably adapted for flush and sealing engagement to the interior wall of the second rod 58. The third rod 70 is preferably adapted for vertical movement within the cylinder 28 and the second rod 58, and is limited in vertical expansion by the engagement between the third platform 72 and the third circular ledge 66 of the second top portion 64. During the introduction of saline solution or water into the cylinder 28, the third rod 70 expands vertically upward due to the internal pressure of the fluid. The vertical expansion of the third rod 70 is terminated upon the engagement between the third platform 72 and the third circular ledge 66. It should be noted that the third platform 72 and the third O-ring 78 provide a seal against the interior of the second rod 58 preventing saline solution or water from leaking from the means for expansion 14. It should also be noted that the second rod 58 functions as a cylinder, confining the expansion of the third rod 70 during use of the mechanical tissue expansion appliance 10.

As seen in FIG. 2, the third platform 72 and the third O-ring 78 are adapted for engagement to the interior wall of the second rod 58, and to the base portion 32 of the cylinder 28 when the mechanical tissue expansion appliance 10 is in its fully retracted or non-expanded position.

The purpose of the first, second and third telescoping rods 46, 58 and 70, respectively, is to expand from the cylinder 28 upon the introduction of saline solution or water into the removable mechanical tissue expansion appliance 10. The telescopic expansion of the first, second, and third rods 46, 58 and 70, respectively, separates the pair of tissue expansion plates 12 for incremental enlargement of the cavity 20. The enlargement of the cavity 20 permits additional ingrowth of natural fatty, glandular, or mammary tissue through the plurality of first, second and third apertures 22, 24 and 26, respectively, for the permanent filling of the cavity 20 with natural tissue, thereby eliminating the necessity of a permanent prosthetic implant. Alternatively, the expansion of the cavity 20 may be filled with natural fatty or other tissue transplanted from another area of a person's body. Rejection and/or infection associated with the filling of the cavity 20 is thereby minimized.

The base portion 32 of the cylinder 28 preferably includes a channel 38. The channel 38 preferably includes a lip 40 having a threaded receiving surface. The threaded receiving surface of the lip 40 preferably functions as an inlet 80 for the channel 38. The inlet 80 is preferably adapted for receiving engagement of a threaded penetrating outlet 82 of the operating means 16. Alternatively, the inlet 80 may be of any type as preferred by an individual including, but not limited to, membranes adapted for receipt of fluid from a source such as syringe and/or a barbed fitting for direct receiving engagement of a fluid supply hose.

In the preferred embodiment, a one-way check valve 84 is positioned in the channel 38 between a spring means 86 and the inlet 80. The one-way check valve 84 preferably includes a cylindrical plug 88 which may be suitably formed of silicone material. In the preferred embodiment, the base portion 32 of the cylinder 28 includes a pocket 90 for the holding of the spring means 86. The spring means 86 is preferably a spring. The pocket 90 is preferably aligned to the channel 28 and to the inlet 80. The cylindrical plug 88 is preferably positioned in the channel 38 between the spring means 86 and the inlet 80. The cylindrical plug 88 preferably has the same diameter dimension as the channel 38. As saline solution and/or water is forcibly introduced through the inlet 80 into the channel 38, the pressurized fluid actuates the cylindrical plug 88 toward the pocket 90 compressing the spring means 86. Preferably the cylindrical plug 88 is compressed toward the pocket 90 for a distance sufficient to establish a fluid flow course through the channel 38 into the cylinder 28. Continued introduction of fluid through the inlet 80 then vertically expands the first, second, and third rods 46, 58 and 70 from the cylinder 28, incrementally expanding the tissue expansion plates 12 against mammary tissue for enlargement of the cavity 20. As the supply of the fluid is terminated, the spring means 86 actuates the cylindrical plug 88 toward the inlet 80, closing the channel 38 and ceasing communication between the cylinder 28 and the operating means 16.

It should be noted that any type of spring means 86 may be used at the preference of an individual provided that the spring means 86 selected may be suitably compressed for opening of the channel 38 for fluid flow communication between the cylinder 28 and the operating means 16. The spring means 86 is also required to expand and actuate the cylindrical plug 88 for the closing of the channel 38 when the flow of fluid into the inlet 80 is ceased.

Alternatively, any one-way valve may be selected for use within the channel 38 as preferred by an individual. As seen in FIG. 4, an alternative duckbill-type of one-way valve 92 is depicted. In this embodiment, following the introduction of saline solution or water into the inlet 80, the duckbill valve 92 is actuated toward a closed configuration within the pocket 90, opening a fluid flow course from the channel 38 to the cylinder 28 for telescopic expansion of the first, second and third rods 46, 58 and 70, respectively. (FIG. 4) As fluid pressure is applied to actuate the duckbill valve 92 into a closed configuration, a fluid flow course into the cylinder 28 is established. Upon termination of fluid pressure, the duckbill valve 92 expands outwardly along the slot 93, opening to seal against the interior of the pocket 90, terminating communication between the operating means 16 and the cylinder 28. The duckbill valve 92 prevents pressure leaks in a supply tubing or port during high pressure conditions which are caused by axial forces exerted on the cylinder 28.

Figure 5:
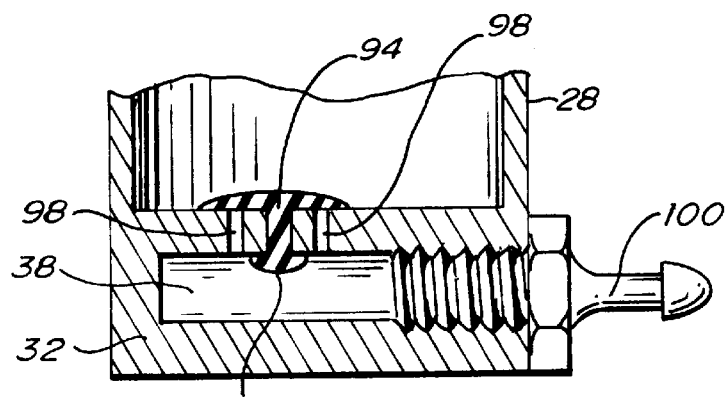
FIG. 5 is a detail view of an umbrella valve.

Alternatively, as seen in FIG. 5, an umbrella-type of one-way valve 94 is depicted. In this embodiment, following the introduction of saline solution or water into the inlet 80, the umbrella valve 94 is actuated upward expanding a lower tab unit 96, for the opening of a fluid flow course through the channel 38 and a pair of connection channels 98 to the cylinder 28, for telescopic expansion of the first, second and third rods 46, 58 and 70. In this embodiment, the lower tab unit 96 is positioned within the channel 38, and the umbrella portion of the umbrella valve 94 is preferably positioned within cylinder 28 proximal to the base portion 32. As fluid pressure is applied from the channel 38 to actuate the umbrella one-way valve 94 upwards toward the cylinder 28, the lower tab unit 96 is flattened or expanded. Upon termination of fluid pressure upon the lower tab unit 96, the lower tab portion 96 expands returning the umbrella portion to a covering relationship over the pair of connection channels 98, terminating communication between the operating means 16, the channel 38, and the cylinder 28.

As depicted in FIG. 5, the inlet 80 preferably includes a penetrating fitting 100 for insertion into a supply tubing hose of the operating means 16. In this embodiment, a clamp 108 may be used to securely affix the supply tubing or hose to the penetrating fitting 100 of the inlet 80 to insure a sealing engagement, thereby preventing leakage of saline solution or water into an individual. It should be noted that the fluid pressure exerted upon the penetrating fitting 100 may exceed 10 psi.

In the preferred embodiment, the operating means 16 is connected in fluid flow relationship to the means for expansion 14. Alternatively, the operating means 16 may be connected to the means for expansion 16 by mechanical means as hereinafter described.

In the preferred embodiment, the operating means 16 includes a supply port 102 having a membrane 104, a supply tube/hose 106, and an outlet 82. In the preferred embodiment, the supply/tube hose 106 is preferably affixed to the supply port 102 and to the outlet 82 by clamps 108. The outlet 82 preferably includes a threaded penetrating member adapted for engagement into the threaded receiving member of the inlet 80. Alternatively, the supply/hose 106 may be suitably connected to an inlet 80 having a penetrating fitting 100 via a clamp 108, provided that a seal is created preventing leakage when the operating means 16 is exposed to fluid pressures in excess of 10 psi.

The supply tube/hose 106 may be constructed or formed of any preferred material provided that the essential features, functions, and attributes described herein are not sacrificed. The supply tube/hose 106 is preferably formed for medical and/or surgical applications and is able to withstand, without fracture or fail, fluid flow pressures in the range of 10 psi. The length of the hose 106 may vary at the discretion of an individual for the convenient positioning of the supply port 102 at a location exterior to the breast of an individual. The supply tube/hose 106 may be of any desired length for positioning of the supply port 102 under the arm of an individual, or may be suitably longer for positioning of the supply port 102 proximal to the waist of an individual. It should be noted that the supply port 102 may be preferably positioned for subdermal injection of saline and/or water at the discretion of a physician. Alternatively, the supply port 102 may be connected to an implantable infusion pump or an external infusion pump at the discretion of an individual or physician. The subdermal injection port 102 provides a physician with the ability to use a needle and a syringe to periodically inject fluids into the operating means 16 from beneath the patient's skin for filling of the hydraulic cylinder 28. Alternatively, the hose/tubing 106 may be connected to an implantable infusion pump or an external infusion pump in order to achieve a more controlled and gradual expansion of the removable mechanical tissue expander appliance 10.

The supply port 102 is preferably formed of stainless steel metal material. Alternatively, the supply port 102 may be formed of any material as preferred by an individual including, but not limited to, the use of other metal materials and/or plastic. In the preferred embodiment, the supply port 102 includes a silicone membrane 104 which is suitably adapted for receiving engagement of injections of saline solution or water through a syringe. The supply port 102 preferably includes a base portion and a cylindrical portion and may be suitably varied to any dimensional shape or size as preferred by a physician or an individual. The membrane 104 is preferably adapted for repeated penetration by a syringe during the supply of saline solution or water for enlargement of the removable mechanical tissue expansion appliance 10. The membrane 104 is preferably adapted for sealing of the supply port 102 from leaks following the periodic injection with saline or other suitable fluids. The membrane 104 is preferably adapted to sustain a seal following repeated injections with fluid for enlargement of the removable mechanical tissue expansion appliance 10.

It should be noted that the operating means 16 is preferably connected in fluid flow relationship to the cylinder 28 via the channel 38. The operating means 16 thereby provides a mechanism for transfer of incremental power to the means for expansion 14, for incremental enlargement of a cavity 20 or void which is preferably filled by the ingrowth of natural human tissue during the reconstruction or augmentation of a breast.

It should also be noted that the operating means 16 is releasably engaged to the inlet 80 such that disassembly and removal of the mechanical tissue expansion appliance 10 from a body is facilitated.

As seen in FIG. 3, the saline solution or water introduced into the supply port 102 traverses the hose/tubing 106 for engagement into the removable mechanical tissue expansion appliance 10 via the inlet 80. The fluid and associated pressure therein actuates the one-way check valve 84 for opening communication between the operating means 16 and the cylinder 28. Fluid then flows through the channel 38 into the cylinder 28 for expansion of the first, second and third rods 46, 58 and 70, and the tissue expansion plates 12. Initially, it is expected that the first rod 46 expands outwardly from the interior of the cylinder 28 until engagement occurs between the first platform 48 and the first circular ledge 44. As additional fluid is introduced into the cylinder 28, the internalized increase in pressure expands the second rod 58 from the cylinder 28. It is expected that the second rod 58 expands outwardly from the cylinder 28 until such time as the second platform 60 embraces the second circular ledge 54, thereby initiating the expansion of the third rod 70 from the cylinder 28. At such time as the third platform 72 engages the third circular ledge 66 of the threaded cap 36, maximum expansion of the rods from the cylinder 28 has occurred.

Figure 6:
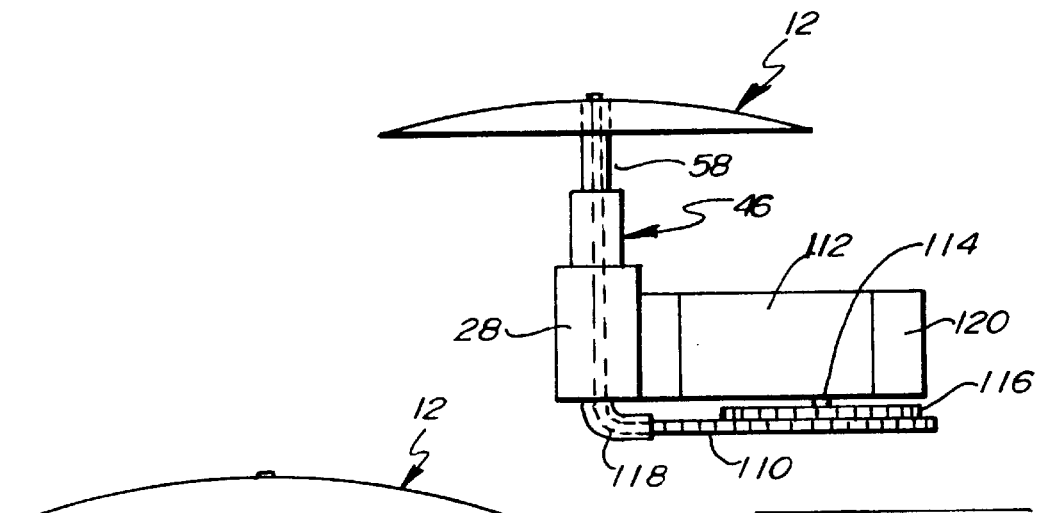
FIG. 6 is a detail view of the flexible threaded arm, gear, and cylinder for the means for expansion.

In an alternative embodiment as depicted in FIG. 6, the means for expansion 14 includes a rotatable flexible threaded arm 110 which is preferably attached to the third rod 70. The rotatably flexible threaded arm 110 is preferably engaged to the base portion 32 of the cylinder 28 via a guide 118. The rotatable flexible threaded arm 110 is preferably engaged to a gear 116 which in turn is affixed to a drive shaft 114 depending from a motor 112. The motor 112 is operated by a control 120. In this embodiment, the manipulation of the control 120 activates the motor 112 for rotation of the drive shaft 114 and gear 116. The rotation of the gear 116, as engaged to the rotatably flexible threaded arm 110, causes the vertical expansion of the third rod 70 from the cylinder 28. The engagement of the third platform 72 to the third circular ledge 66 results in the expansion of the second rod 58 from the cylinder 28. The continued expansion of the second rod 58 outwardly from the cylinder 28 results in the engagement between the second platform 60 and the second circular ledge 54. Continued rotation of the rotatable flexible threaded arm 110 then causes the expansion of the first rod 46 outwardly from the cylinder 28 until such time as the first platform 48 engages the first circular ledge 44 of the threaded cap 36. Further expansion of first, second and third rods 46, 58 and 70 from the cylinder 28 is then terminated via a safety mechanism. Rotation of the motor 112 in the opposite direction draws the rotatably flexible arm 110, via the gear 116, in a downward direction pulling the third rod 70 toward the cylinder 28. Engagement between a tissue expansion plate 12 and the second rod 58 causes the retraction of the second rod 58 within the cylinder 28. Engagement of the tissue expansion plate 12 and the first rod 46 causes the retraction of the first rod 46 within the cylinder 28. It should be noted that the control 120 preferably regulates the incremental enlargement of the removable mechanical tissue expansion appliance 10. In this embodiment, the control 120 may be preferably operated by an electrical switch and/or radio operated means at the preference of an individual. Alternative means of control 120 may be implemented at the preference of an individual provided that the essential functions, features and attributes described herein are not sacrificed.

Figure 7:
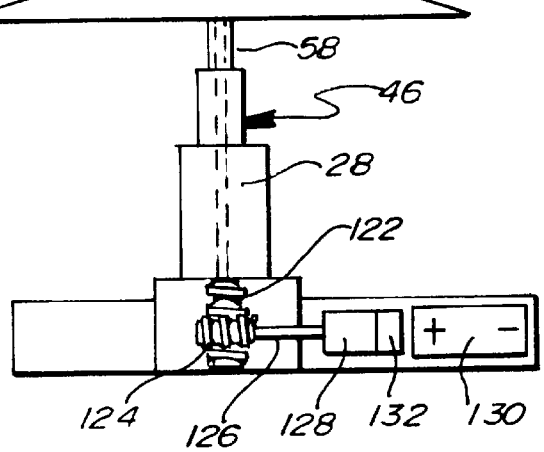
FIG. 7 is a detail view of the worm gear, spur gear, and cylinder for the means for expansion.

In an alternative embodiment as depicted in FIG. 7, the means for expansion 14 includes the elements of a worm gear 122, a spur gear 124, a shaft 126, a motor 128, a battery 130, and a control 132. In this embodiment, the first, second and third rods 46, 58 and 70 include a keyed threaded surface (not shown). The worm gear 122 is engaged to the keyed threaded surface. The rotation of the worm gear causes the telescopic expansion of the first, second, and third rods 46, 58 and 70 from the cylinder 28, without rotation of the first, second and third rods 46, 58 and 70 with respect to the cylinder 28. Rotation of the first, second and third rods 46, 58 and 70, and rotation of the tissue expansion plates 12 is highly undesirable. The worm gear 122 is preferably engaged to a spur gear 124 within the base portion 32. The spur gear 124 includes a shaft 126 which extends from the base portion 32 to a motor 128. The motor 128 is preferably electrically connected to a battery 130 and is connected to a control 132. Upon manipulation of the control 132, power is supplied from the battery 134 for engagement of the motor 128 which causes the rotation of the shaft 126 and spur gear 124. Incremental engagement of the control 132 thereby causes incremental enlargement of the removable mechanical tissue expansion appliance 10 for expansion of a cavity 20 during reconstruction and/or augmentation of a breast. It should be noted that the motor 128 is rotatable in two directions. Therefore, reversal of the direction of the shaft 126 rotates the spur gear 124 in the opposite direction, thereby retracting of the first, second and third rods 46, 58 and 70, and tissue expansion plates 12.

Figure 8:
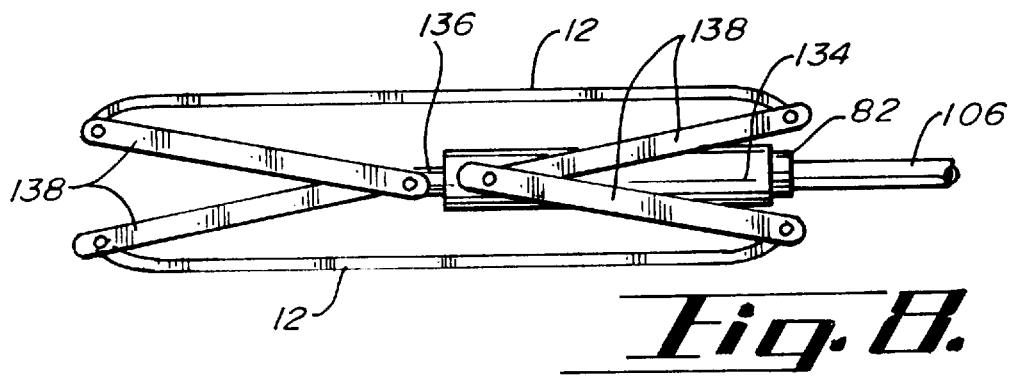
FIG. 8 is a detail view of a hydraulic cylinder and expansible linkages in a retracted position.
Figure 8A:
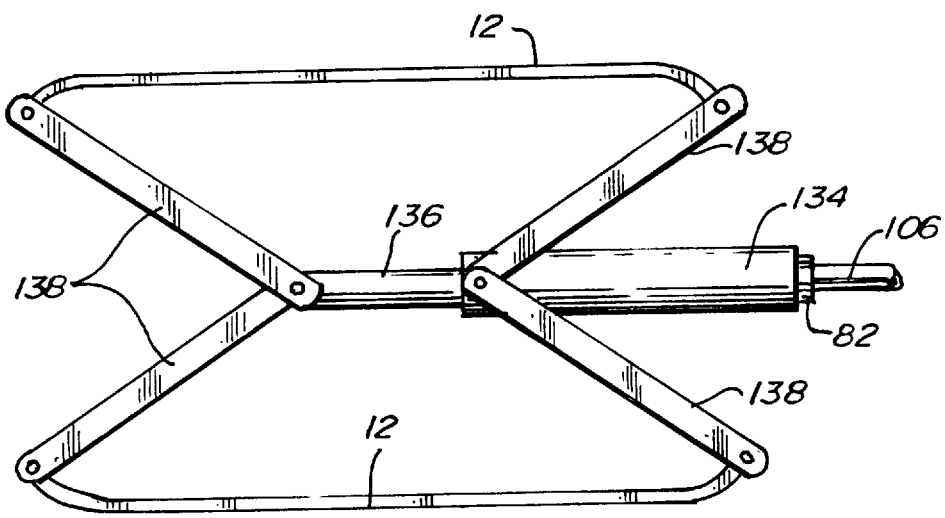
FIG. 8A is a detail view of a hydraulic cylinder and expansible linkages in an expanded position.

An alternative embodiment is depicted in FIGS. 8 and 8A showing a means for expansion 14 which includes an expandable hydraulic cylinder 134 having a piston 136 and a pair of expansible linkages 138. In this embodiment, the expansion of the hydraulic cylinder 134 causes the telescopically outward movement of the piston 136. The outward movement of the piston 136, from the cylinder 134, causes the expansion of the pair of expansible linkages 138 for incremental enlargement of the tissue expansion plates 12, and incremental expansion of a cavity 20. In this embodiment, the expansible linkages 138 are preferably formed of metallic material of sufficient strength and durability to not bend or fail during the expansion of the piston 136 from the hydraulic cylinder 134. In this embodiment, the expansible linkages 138 are preferably pivotally attached to the pair of tissue expansion plates 12, the expandable hydraulic cylinder 134, and the piston 136. The pivotal engagement of the pair of expansible linkages 138 to the pair of tissue expansion plates 12, piston 136, and expandable hydraulic cylinder 134 permits incremental and uniform enlargement of the cavity 20. It should be noted that during operation of the expandable hydraulic cylinder 134, the cavity 20, as a whole, is regularly and uniformly enlarged. The pair of expansible linkages 138 are affixed to the piston 136 and to the expandable hydraulic cylinder 134 to uniformly expand the tissue expansion plates 12. In this embodiment, it should also be noted that the operating means 16 may be suitably affixed to the expandable hydraulic cylinder 134. The expandable hydraulic cylinder 134 may alternatively include either a one-way check valve 84, duckbill-type of one-way valve 92, or umbrella-type of one-way valve 94 at the preference of an individual.

The removable mechanical tissue expansion appliance 10 is preferably retracted into its smallest configuration prior to its surgical introduction into an individual. The removable mechanical tissue expansion appliance 10 is then suitably inserted into mammary tissue for expansion and/or reconstruction thereof. Following insertion of the removable mechanical tissue expansion appliance 10 into an individual, the outlet 82 of the operating means 16 may be preferably screwed into the inlet 80 of the cylinder 28. At that time, any incision may be surgically closed. Incremental expansion of the removable mechanical tissue expansion appliance 10 may then occur by the introduction of saline solution or water via the supply port 102 and membrane 104. The removable mechanical tissue expansion appliance 10 may then be incrementally enlarged for the stretching of mammary tissue about an area to be reconstructed and/or augmented. At such time as expansion of mammary tissue has occurred to a desired level, the removal of the operating means 16 from the cylinder 28 may occur by rotation of the hose/tubing 106, such that the outlet 82 is disengaged from the inlet 80. Withdrawal of the operating means 16 may then occur. The removable mechanical tissue expansion appliance 10 is then retained within an individual for a desired duration of time, permitting the ingrowth of natural fatty, glandular, or mammary tissue through the plurality of first, second or third apertures 22, 24 and 26, respectively, for filling of the cavity 20. At such time as the ingrowth of natural tissue has filled the cavity 20, the incision through the mammary tissue may be reopened for retraction of the removable mechanical tissue expansion appliance 10. At that time, a drainage hose/tubing may be integrally attached to the inlet 80 for the release of internal fluid pressure from the cylinder 28. Manipulation of the one-way check valve 84 is required, necessitating the movement of the cylindrical plug 88 into the pocket 90. A surgeon may then preferably remove the retaining rings 18 which affix the pair of tissue expansion plates 12 to the means for expansion 14. The tissue expansion plates 12 may then be suitably withdrawn. The first, second and third rods 46, 58 and 70 as retracted into the cylinder 28 may then be removed. The close of the incision may then surgically occur. It should be noted that in the preferred embodiment that all of the elements of the removable mechanical tissue expansion appliance 10 are formed of stainless steel metal insuring convenient verification of withdrawal through the use of X-rays. The removable mechanical tissue expansion appliance 10 significantly enhances the safety and health of an individual by eliminating the problems of encapsulation, contracture, rejection, and/or infection of foreign prosthetic implants within the breast of an individual.

The present invention may be embodied in other specific forms without departing from the spirit or essential attributes thereof; therefore, the illustrated embodiment should be considered in all respects as illustrative and not restrictive, reference being made to the appended claims rather than to the foregoing description to indicate the scope of the invention.

What is claimed:

1. A removable mechanical tissue expansion appliance comprising a pair of tissue expansion plates mounted to a means for incremental expansion for separating said tissue expansion plates outwardly from each other for establishment of a cavity whereby said cavity is filled with ingrowth over time of natural tissue for permanent tissue expansion, said means for expansion comprising:
    (a) a cylinder and at least two rods telescopically engaged to each other and to said cylinder, said cylinder having a channel and a valve in flow communication therewith;
    (b) an operating means in flow communication with said channel for incremental expansion of said rod from said cylinder; and
    (c) a spring means for actuating said valve into a sealed and closed position terminating communication between said cylinder and said operating means.

2. The removable mechanical tissue expansion appliance according to claim 1, said operating means comprising a hose having an outlet and a port, said outlet engaging said channel, said port comprising a membrane for receipt of incremental portions of saline solution or water for communication through said hose for incremental expansion of said rod from said cylinder, and incremental expansion of said tissue expansion plates for incremental enlargement of said cavity.

3. The removable mechanical tissue expansion appliance according to claim 1, wherein said valve is a one-way check valve having a cylindrical plug for sealing and terminating communication between said cylinder and said operating means.

4. The removable mechanical tissue expansion appliance according to claim 1, wherein said means for expansion receives water or saline solution for telescopic expansion of said rod from said cylinder.

5. The removable mechanical tissue expansion appliance according to claim 4, wherein said channel further comprises an inlet.

6. The removable mechanical tissue expansion appliance according to claim 5, wherein said operating means further comprises an outlet engaged to said inlet for receipt of incremental portions of saline solution or water for telescopic expansion of said rod from said cylinder.

7. The removable mechanical tissue expansion appliance according to claim 3, wherein said spring means further comprises a spring engaged to said cylindrical plug for sealing communication between said cylinder and said operating means.

8. The removable mechanical tissue expansion appliance according to claim 1, said means for expansion comprising:
    (a) a cylinder and a rod telescopically engaged within said cylinder, said cylinder having a channel having an umbrella-shaped one-way valve within said cylinder; and (b) an operating means communicating with said channel for incremental enlargement of said cylinder.

9. The removable mechanical tissue expansion appliance according to claim 1, further comprising:

a third rod having a diameter smaller than each of said at least two rods telescopically engaged within, and sealed to, one of said at least two rods for vertical expansion therefrom for incremental enlargement of said cavity.

10. A removable mechanical tissue expansion appliance comprising:

(a) a pair of tissue expansion plates where one of said tissue expansion plates is mounted to a cylinder;

(b) a first rod having a diameter telescopically engaged within, and sealed to, said cylinder for vertical expansion therefrom for incremental enlargement of said cavity;

(c) a second rod having a diameter smaller than said first rod, telescopically engaged within, and sealed to, said first rod for vertical expansion therefrom for incremental enlargement of said cavity;

(d) a third rod having a diameter smaller than said second rod, telescopically engaged within, and sealed to, said second rod for vertical expansion therefrom for incremental enlargement of said cavity;

(e) the other tissue expansion plate being mounted to said third rod;

(f) an operating means communicating with said cylinder for expansion of said first, second, and third rods, said operating means being releasably sealed for incremental expansion of said first, second, and third rod and incremental enlargement of said cavity, where said cavity is filled with ingrowth of natural tissue for permanent tissue expansion;

(g) a channel having a valve communicating with said cylinder and said operating means; and (h) a spring means for actuating said valve into a sealed and closed position terminating communication between said cylinder and said operating means.

11. A removable mechanical tissue expansion appliance comprising:

(a) a pair of tissue expansion plates where one of said tissue expansion plates is mounted to a cylinder;

(b) a first rod having a diameter telescopically engaged within, and sealed to, said cylinder for vertical expansion therefrom for incremental enlargement of said cavity;

(c) a second rod having a diameter smaller than said first rod, telescopically engaged within, and sealed to, said first rod for vertical expansion therefrom for incremental enlargement of said cavity;

(d) a third rod having a diameter smaller than said second rod, telescopically engaged within, and sealed to, said second rod for vertical expansion therefrom for incremental enlargement of said cavity;

(e) the other tissue expansion plate being mounted to said third rod;

(f) an operating means having an outlet, a hose, and a port having a silicone membrane for receipt of incremental portions of saline solution or water for telescopic expansion of said rods from said cylinder, said operating means for communicating with said cylinder for incremental enlargement of said cavity where said cavity is filled with ingrowth of natural tissue for permanent tissue expansion;

(g) a channel having a valve communicating with said cylinder and said operating means; and (h) a spring means for actuating said valve into a sealed and closed position terminating communication between said cylinder and said operating means.

12. A removable mechanical tissue expansion appliance comprising a pair of tissue expansion plates mounted to a means for incremental expansion for separating said tissue expansion plates outwardly from each other for establishment of a cavity whereby said cavity is filled with ingrowth over time of natural tissue for permanent tissue expansion, wherein each of said pair of tissue expansion plates further comprises a plurality of apertures for passing engagement of natural tissue for ingrowth within said cavity.

13. The removable mechanical tissue expansion appliance according to claim 12, wherein said tissue expansion plates are arcuate in shape.

\* \* \* \* \*